(12) United States Patent
McClintock

(10) Patent No.: US 7,976,512 B2
(45) Date of Patent: Jul. 12, 2011

(54) SYRINGE CONTROL PISTOL

(76) Inventor: Scott Andrew McClintock, Murrieta, CA (US)

( * ) Notice: Subject to any disclaimer, the term of this patent is extended or adjusted under 35 U.S.C. 154(b) by 367 days.

(21) Appl. No.: 12/316,849

(22) Filed: Dec. 16, 2008

(65) Prior Publication Data

US 2010/0152675 A1   Jun. 17, 2010

(51) Int. Cl.
*A61M 5/315* (2006.01)
(52) U.S. Cl. .................................... 604/228; 604/227
(58) Field of Classification Search .............. 604/211, 604/218, 224, 227, 228, 232–235
See application file for complete search history.

(56) References Cited

U.S. PATENT DOCUMENTS

| | | | |
|---|---|---|---|
| 2,074,401 A | 3/1937 | Kauzal | |
| 3,238,941 A | 3/1966 | Klein et al. | |
| D287,279 S | 12/1986 | Lazickas | |
| D300,851 S | 4/1989 | Grieshaber | |
| 5,408,919 A | 4/1995 | Hutzler et al. | |
| D370,064 S | 5/1996 | Livneh | |
| 5,591,135 A * | 1/1997 | Sullivan | 604/211 |
| D383,839 S | 9/1997 | Sullivan | |
| D412,746 S | 8/1999 | Pasini | |
| D458,368 S | 6/2002 | Berberich et al. | |
| D465,281 S | 11/2002 | Lang | |
| D466,936 S | 12/2002 | Shaw et al. | |
| 6,565,538 B2 | 5/2003 | Quinn et al. | |
| 6,616,634 B2 | 9/2003 | Benz et al. | |
| D497,204 S | 10/2004 | Von Amende et al. | |
| D497,427 S | 10/2004 | Hickingbotham | |
| D562,978 S | 2/2008 | Garito et al. | |
| D576,273 S | 9/2008 | McClintock et al. | |

* cited by examiner

*Primary Examiner* — Kevin C Sirmons
*Assistant Examiner* — Larry R Wilson
(74) *Attorney, Agent, or Firm* — Palomar Patent; Calif Tervo

(57) ABSTRACT

A syringe control pistol for holding in a user's hand to control the dispensing of fluid from a syringe generally includes front and rear arms pivotly connected at their bottom ends. The front arm includes a front face for receiving pressure from the fingers of the user's hand and a top end including a barrel holder for holding the barrel of the syringe such that its barrel cannot move forward and its plunger extends rearward. The rear arm includes a rear face for receiving pressure from the user's palm and a top end including a roller for bearing against the bearing surface of the plunger for pushing the plunger forward in the barrel to disperse fluid from the syringe as the user's hand squeezes front and rear arms toward one another. A plurality of barrel holders for holding syringes of different sizes is selectively attachable to the front arm.

15 Claims, 6 Drawing Sheets

SYRINGE CONTROL PISTOL

FIELD OF THE INVENTION

This invention relates in general to devices to aid in the use of a syringe, and more specifically involves a pistol-like syringe holder for controlling syringe output.

BACKGROUND OF THE INVENTION

Syringes are used to expel a fluid through an orifice, such through a nozzle, or tubing, or cannula, such as a hypodermic needle.

FIG. 3 of the drawings shows, in phantom, a side elevation view of a common syringe 80. Syringe 80 generally includes a barrel 81 and a plunger 90. Barrel 81 includes walls 82 forming a tube surrounding a lumen 83 for holding the fluid, a closed front end 84 including an orifice 85 for expelling the fluid, and an open rear end 87 defining a rear orifice 88 and having an outwardly extending flange 89 around rear orifice 88. Front orifice 85 typically includes an attachment or collar 86 for attachment of a hypodermic needle, tubing, or nozzle 99.

Plunger 90 includes a front end 91 disposed in lumen 83 of barrel 81, a midsection 93 disposed in rear orifice 88 of barrel 81, and a rear end 94 including a rear-facing, bearing surface 95. Front end 91 may have a seal, such as O-ring 92 for sealing between plunger 90 and barrel walls 82. Syringe 80 has a horizontal center axis 96 midway between the top and bottom of the syringe.

Typically, in use, barrel 81 is held with one hand while fingers of the other hand are placed on the front of flange 89 and the thumb of the other hand is placed on bearing surface 95 of plunger 94. The finger and thumb are squeezed together to force plunger 90 further into barrel 81 to expel the fluid.

Mixing syringes have two or more separate lumens for holding reactive components, that is, components that must be mixed in a precise ration and that change their chemical or physical nature upon mixing. It is common to design the mixing syringe such that pressing plunger 90 dispenses all components simultaneously in the correct ratio. The components begin mixing as they exit their respective nozzles. Two-part epoxy is often packaged in such mixing syringes.

One problem with conventional mixing syringes is that care must be taken to depress plunger 90 without applying more pressure to one side than the other so that the ration is correct.

Another problem with mixing syringes is that they often require a large force to expel. Exerting the required force is difficult or impossible for some persons, and it may be difficult to exert the force uniformly during the plunger stroke to evenly distribute the output.

Therefore, there has been a need for a device to aid in the use of mixing syringes.

The safe and effective administration of many types of hypodermic injections by syringe requires sensitive tactile feedback to the administrator. This necessity for tactile feed back is well-know with regard to epidural injections. In epidural injections, the administration attempts to keep a constant force on the plunger while detecting changes in resistance to the flow of fluid. If the resistance goes up, it is a sign that further injection of fluid may cause damage to the patient. Therefore, the administrator is very careful not to exceed the desired force, until the fluid already injected dissipates and the force decreases to the desired force or the administrator moves the tip of the needle slightly to find a more accepting location such that the force decreases to the desired force.

Additionally, the force to the plunger must be applied axially or the apparent resistance increases. It is difficult to apply a purely axial force over the long period of time required for some injections, so false feedback is common.

Therefore, there is a need for a device that aids in providing accurate, sensitive tactile feedback to the administrator of an injection with a syringe.

DETAILED DESCRIPTION OF THE INVENTION

Figure 1:
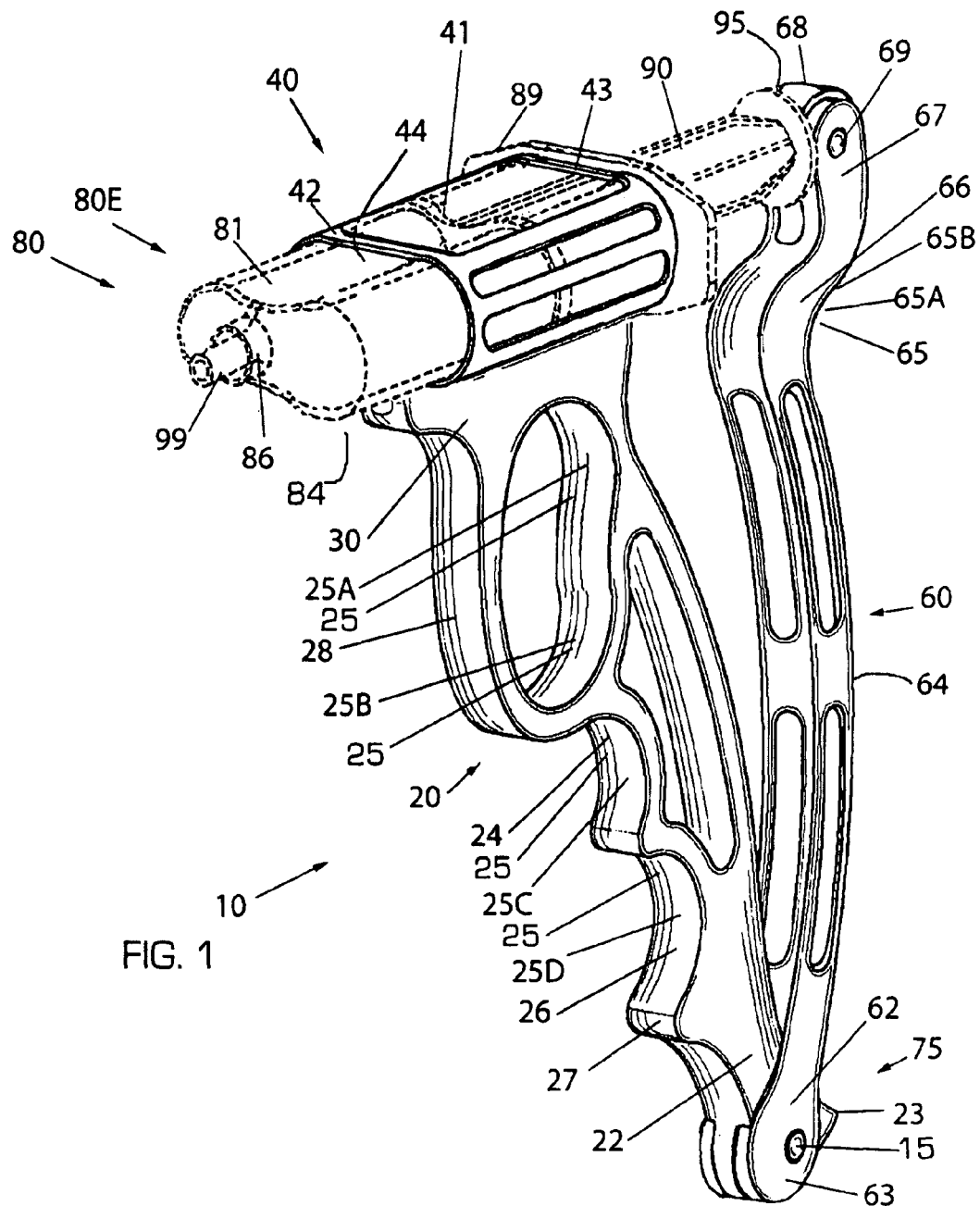
FIG. 1 is a top, left, front, perspective view of an exemplary embodiment of the syringe control pistol of the invention with an epoxy or mixing-type syringe holder showing a mixing-type syringe in phantom.
Figure 2:
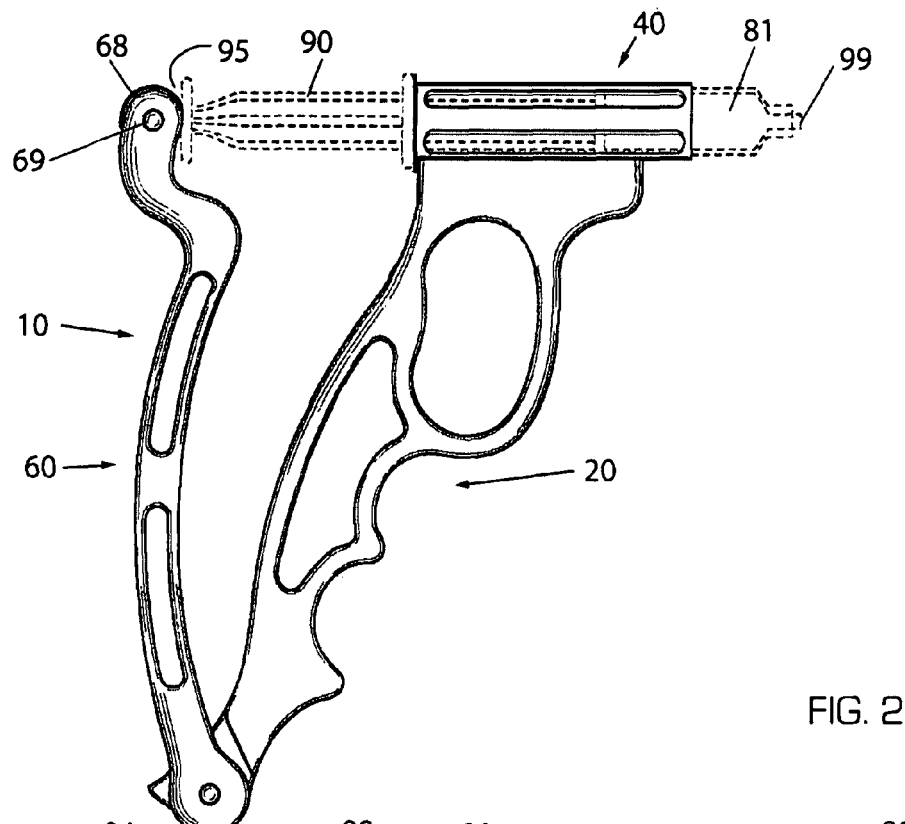
FIG. 2 is a right side elevation view of the pistol of FIG. 1.
Figure 3:
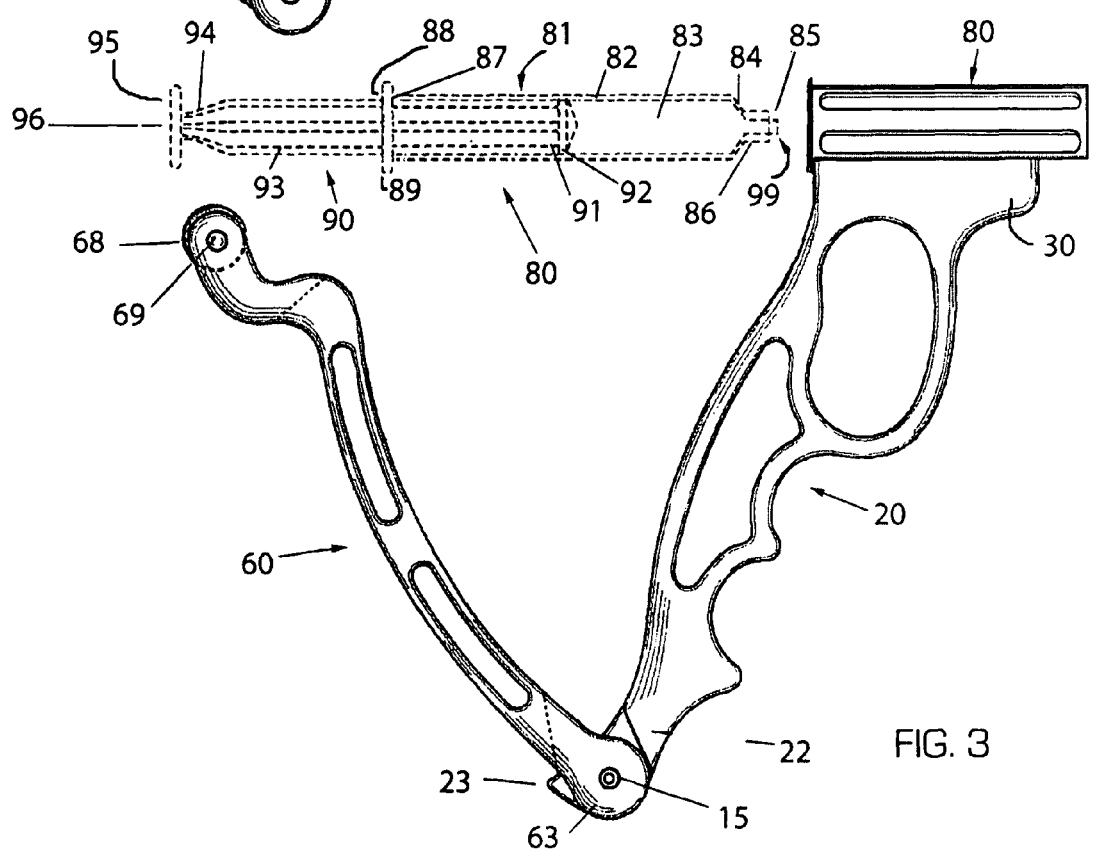
FIG. 3 is a right side elevation view similar to FIG. 2 but with the pistol positioned for receiving a syringe.
Figures 4, 5:
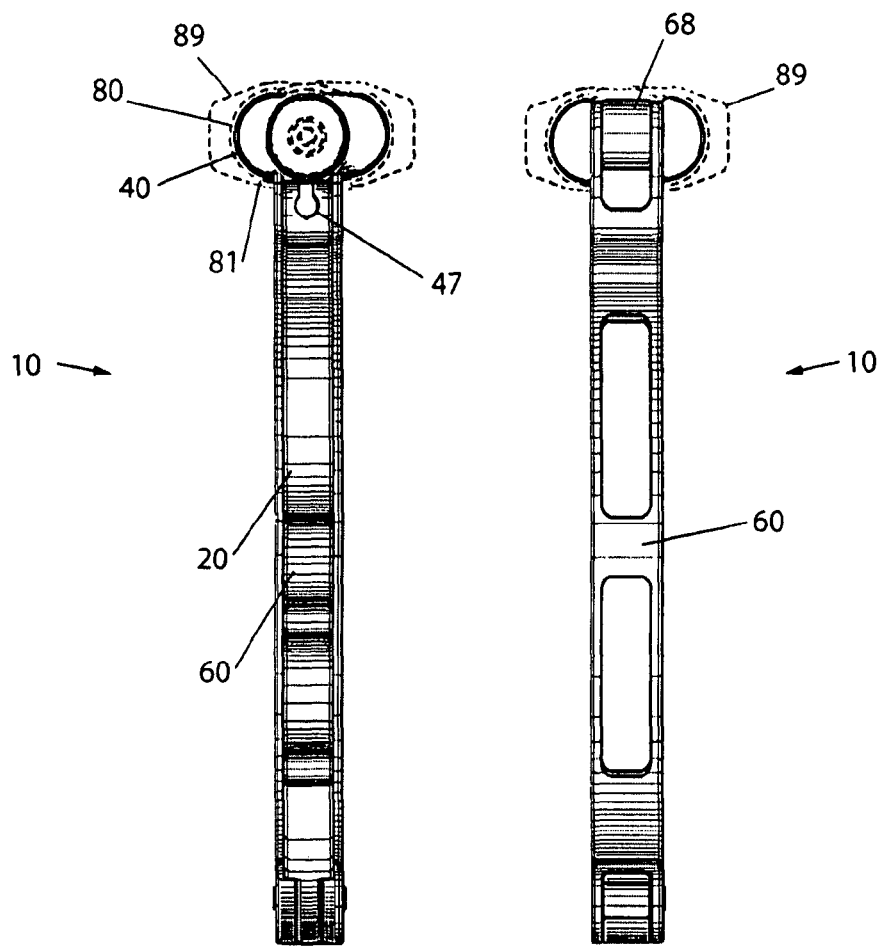
FIG. 4 is a front elevation view of the pistol of FIG. 1.
FIG. 5 is a rear elevation view of the pistol of FIG. 1.
Figure 6:
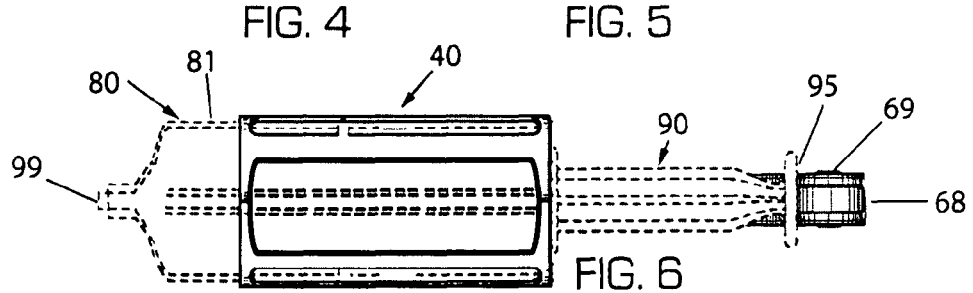
FIG. 6 is a top plan view of the pistol of FIG. 1.
Figure 7:
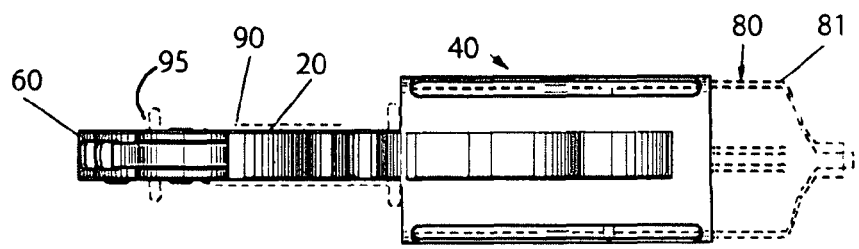
FIG. 7 is a bottom plan view of the pistol of FIG. 1.

With reference now to the drawings, FIGS. 1-7 show an exemplary embodiment of the syringe control pistol 10 of the invention including a holder 40 for holding an epoxy-type or mixing syringe 80E, shown in phantom. FIG. 1 is a top, left, front, perspective view of pistol 10. FIG. 2 is a right side elevation view thereof. FIG. 3 is a right side elevation view similar to FIG. 2 but with pistol 10 positioned for receiving syringe 80. FIG. 4 is a front elevation view thereof of pistol 10 of FIG. 1. FIG. 5 is a rear elevation view thereof. FIG. 6 is a top plan view thereof. FIG. 7 is a bottom plan view thereof.

Syringe control pistol 10 is designed for holding in a hand of a user. Pistol 10 generally includes a front arm 20 and a rear arm 60. Front arm 20 has a bottom end 22, a front face 24 for receiving pressure from the fingers of the user's hand, and a top end 30.

Front face 24 includes a plurality of finger notches 25 for holding the user's fingers at a vertical location. Each notch 25 may include a depression 26 into front face 24 for receiving the finger or a protrusion or rest 27 for supporting a finger or both. Finger notches 25 include a fourth, or index finger notch 25A, a third, or middle finger notch 25B, a second, or ring finger notch 25C, and a first, or little finger notch 25D.

A finger ring 28 surrounds a finger or fingers such that pistol 10 may hang on the surrounded finger or fingers for holding and manipulation of pistol 10. Preferably, finger ring 28 surrounds a plurality of fingers, and preferably at least surrounds index finger notch 25A and middle finger notch 25B, as shown, as this allows the user to apply a moment with one hand to rotate pistol 10 clockwise and counter clockwise as viewed from the side. Such movement is very useful in loading and aiming pistol 10.

A barrel holder 40 is attached to top end 30 of front arm 20 for holding barrel 81 of syringe 80 such that barrel 81 cannot move forward and plunger 90 extends rearward. Holder 40 may be attached in any desirable manner, such as screws or welding, but preferably is selectively attachable and detachable as will be expanded upon later. In the exemplary embodiment, holder 40 includes a tube 41 having front end 42 and a rear end 43. Rear end 43 includes an orifice 44 adapted for receiving barrel 81 from rear end 43 until barrel front end 84 exits tube front end 42 and flange 89 bears against rear end 43. Tube 41 firmly holds barrel 81 in front to rear orientation with pistol 10 and such that barrel 81 can only move rearward.

Rear arm 60 includes a bottom end 62, a rear face 64 for receiving pressure from the palm of the user's hand, and a top end 67.

A hinge or pivoting means, such as pivot pin 15, pivotly connects bottom end 62 of rear arm 60 with bottom end 22 of front arm 20.

Top end 67 includes a roller 68 for bearing against bearing surface 95 of plunger 90 for pushing plunger 90 forward in barrel 81 to disperse fluid from orifice 85 of syringe 80 as the user's hand squeezes top ends 30, 67 of front arm 20 and rear arm 60 respectively toward one another. Because top end 67 of rear arm 60 moves in an arc while pushing plunger 90 into barrel 80, during this movement top end 67 moves vertically on bearing surface 95 of plunger 90. It has been found experimentally that anything less than a freely rolling contact between bearing surface 95 and top end 67, such as by roller 68 mounted on axel 69, creates friction that interferes with the very sensitive tactile pressure feedback desired by the user to determine the accuracy of the injection. Other types of rollers, such as a ball, could be used.

Rear face 64 of rear arm 60 includes a web notch 65 for receiving the web between the user's thumb and index finger and for holding the web at a desired vertical location for efficient and controlled squeezing. Web notch 65 may include a depression 65A into rear face 64 for receiving the web or a protrusion or rest 65B for preventing upward movement of the web, or both.

Top end 67 of rear arm 60 may include a dog leg 66 above notch 65 to move roller 68 sufficiently rearward to encounter bearing surface 95 while leaving notch 65 sufficiently close to front arm 20 such that a user's hand is large enough to squeeze arms 20, 60.

Front arm 20 and rear arm 60 include cooperative stop means 75 for stopping arms 20, 60 from pivoting open past a predetermined angle. In the exemplary embodiment, bottom end 62 of rear arm 60 includes a pair of connecting arms 63 spaced on either side of bottom end 22 of front arm 20 and connected to pivot 15. Front arm 20 pivots between connecting arms 63 and includes a protrusion 23 which encounters rear arm 60 at the base of connecting arms 63 to prevent opening beyond that necessary for insertion or removal of syringe 80.

Figure 9:
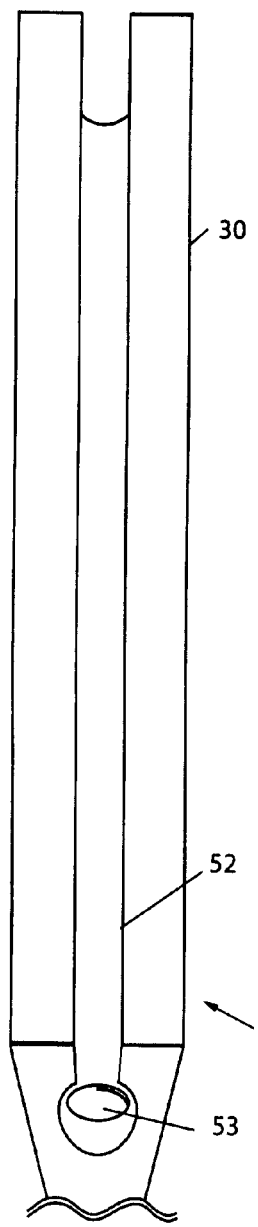
FIG. 9 is partial, top, rear perspective view of the top end of the front arm 20 of FIG. 8.
Figure 10:
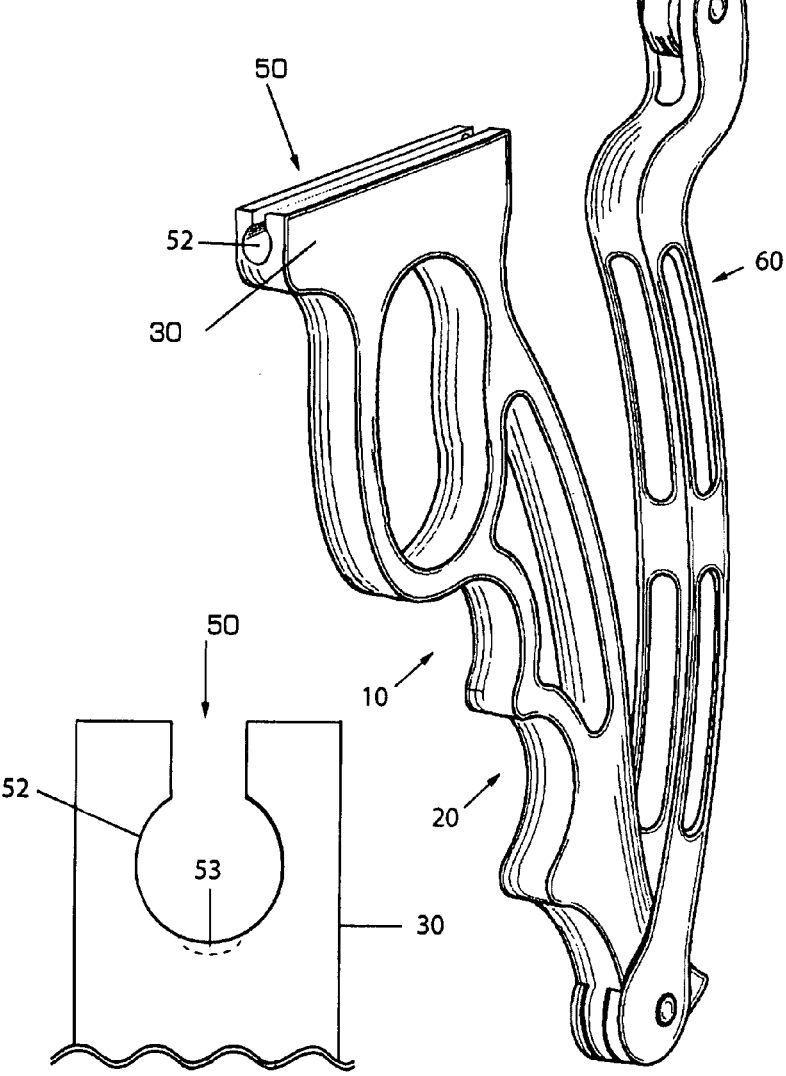
FIG. 10 is a partial, rear elevation view of the top end of front arm of FIG. 9.
Figure 8:
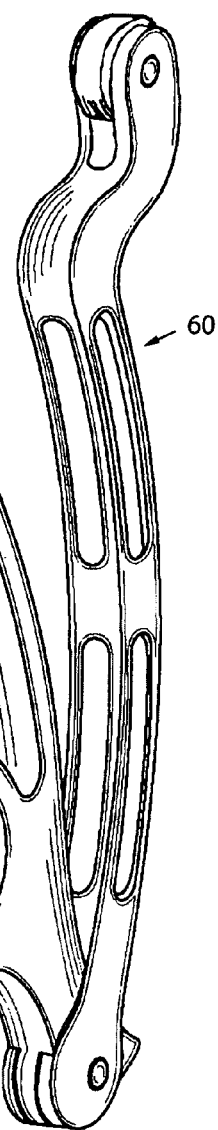
FIG. 8 is a partial, top, front, left side, perspective view of an exemplary embodiment of the top end of front arm.
Figure 11:
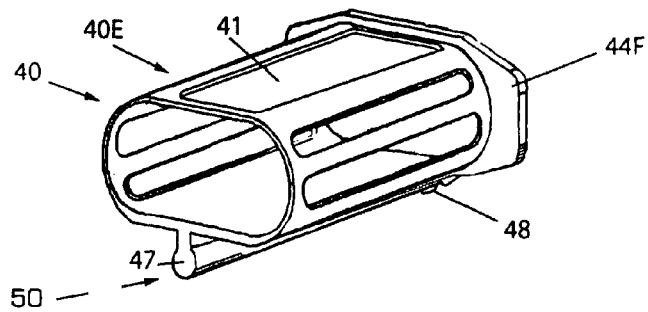
FIG. 11 is a top, left, front perspective view of an exemplary embodiment of the mixing-type barrel holder of FIG. 1.
Figure 12:
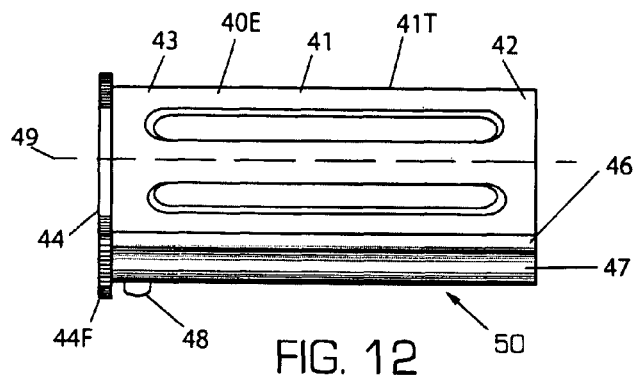
FIG. 12 is a right side elevation view of the barrel holder of FIG. 11.
Figure 13:
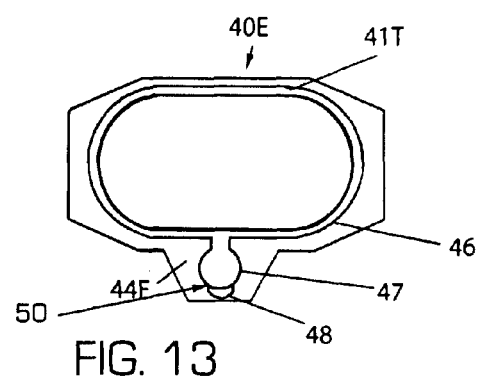
FIG. 13 is a front elevation view of the holder of FIG. 12.
Figure 14:
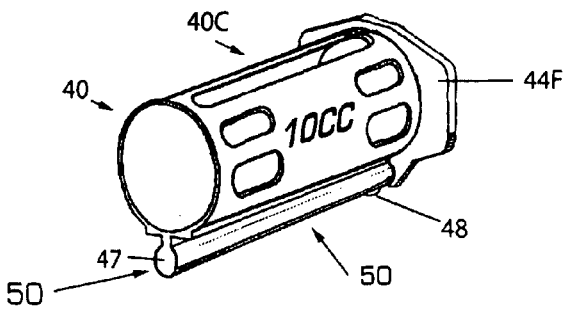
FIG. 14 is a top, left, front perspective view of an exemplary embodiment of a cylindrical barrel holder for the most common size syringe.
Figure 15:
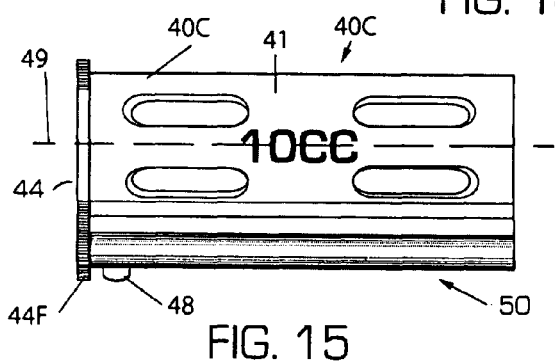
FIG. 15 is a right side elevation view of the barrel holder of FIG. 14.
Figure 16:
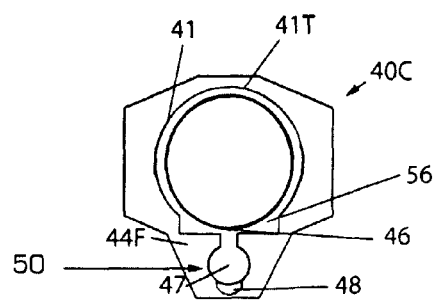
FIG. 16 is a front elevation view of the holder of FIG. 15.
Figure 17:
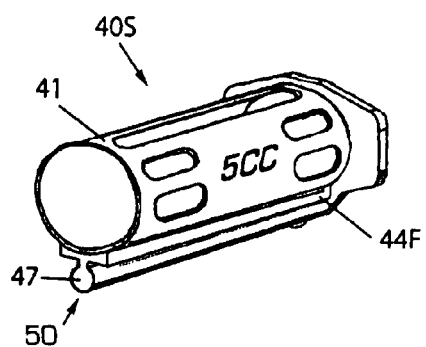
FIG. 17 is a top, left, front, perspective view of an exemplary embodiment of a barrel holder for a smaller than standard size syringe.
Figure 18:
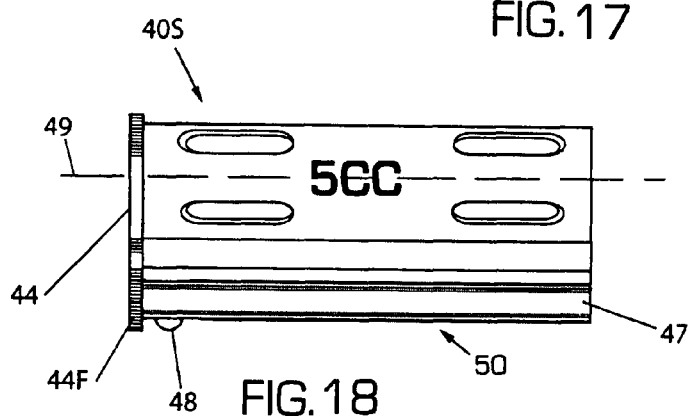
FIG. 18 is a right side elevation view of the barrel holder of FIG. 17.
Figure 19:
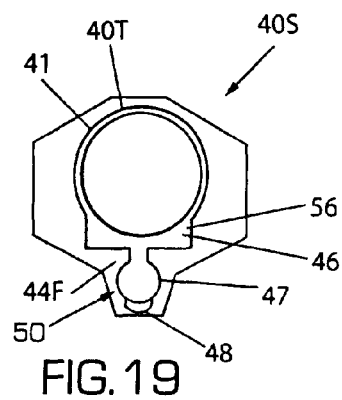
FIG. 19 is a front elevation view of the holder of FIG. 18.

FIGS. 8-19 show exemplary embodiments of a plurality of different barrel holders 40 and cooperative mounting means 50 on holder 40 and top end 30 of front arm 20 for selectively connecting and disconnecting a holder 40 to front arm 20. FIG. 8 is a partial, top, front, left side, perspective view of an exemplary embodiment of top end 30 of front arm 20, FIG. 9 is partial, top, rear perspective view of top end 30 of FIG. 8, and FIG. 10 is a partial, rear elevation view of top end 30 of FIG. 9. FIG. 11 is a top, left, front perspective view of an exemplary embodiment of the mixing-type barrel holder 40E of FIG. 1, FIG. 12 is a right side elevation view thereof, and FIG. 13 is a front elevation view thereof. FIG. 14 is a top, left, front perspective view of an exemplary embodiment of a cylindrical barrel holder 40C for the most common cylindrical syringe 80, FIG. 15 is a right side elevation view thereof, and FIG. 16 is a front elevation view thereof. FIG. 17 is a top, left, front, perspective view of an exemplary embodiment of a small barrel holder 40S for a smaller than standard size syringe 80, FIG. 18 is a right side elevation view thereof, and FIG. 19 is a front elevation view thereof.

Cooperating attachment means 50 includes a front-to-rear sliding attachment, such as semi-circular slide rod 47 on bottom 46 of tube 41, and a rear-to-front sliding attachment, such as mating slide socket 52 on top end 30. Socket 52 and slide rod 47 include cooperating detent means, such as bump 48 on slide rod 47 and mating dimple 53 on socket 52, for resiliently retaining barrel holder 40 on said front arm 20. Other detents, such as a spring biased ball and dimple, as are well-known in the art, may be used.

Each holder 40 has a horizontal center axis 49 midway between top 41T and bottom 46 of tube 41. Preferably, each holder 40 holds syringe 80 such that roller 68 bears on horizontal center axis 96 (see FIG. 3) of plunger 90. To accomplish this, some holders 40, such as 40C, 40S, include a spacer 56 below tube 41 so that center axis 49 of each holder 40 is also substantially in alignment with roller 68.

Preferably, pistol 10 is made of autoclavable materials as well known in the art.

From the foregoing description, it is seen that the present invention provides an extremely simple and reliable device for controlling a syringe.

Although a particular embodiment of the invention has been illustrated and described, various changes may be made in the form, composition, construction, and arrangement of the parts herein without sacrificing any of its advantages. Therefore, it is to be understood that all matter herein is to be interpreted as illustrative and not in any limiting sense, and it is intended to cover in the appended claims such modifications as come within the true spirit and scope of the invention.

I claim:

1. A syringe control pistol for holding in a hand of a user to control the dispensing of fluid from a syringe; the syringe including: a barrel; and a plunger; the barrel including: a front end; and a rear end including an orifice having outward flange around the orifice; the plunger including: a front end disposed in the barrel; a midsection disposed in the orifice; and a rear end including a rear-facing, bearing surface; said pistol including:
    a front arm including:
        a bottom end;
        a front face for receiving pressure from the fingers of the user's hand; and
        a top end:
    a barrel holder attached to said top end of said front arm for holding the barrel of the syringe such that the barrel cannot move forward and the plunger extends rearward;
    a rear arm including:
        a bottom end pivotly connected to said bottom end of said front arm;

a rear face for receiving pressure from the palm of the user's hand; and
a top end including:
a roller for bearing against the bearing surface of the plunger for pushing the plunger forward in the barrel to disperse fluid from the syringe as the user's hand squeezes said front arm and said rear arm toward one another.

2. The syringe control pistol of claim 1 wherein:
said rear arm includes:
a web notch.

3. The syringe control pistol of claim 1 wherein:
said front face includes:
a finger notch.

4. The syringe control pistol of claim 3 wherein:
said rear arm includes:
a web notch.

5. The syringe control pistol of claim 1 wherein:
said front face includes:
a plurality of finger notches.

6. The syringe control pistol of claim 5 wherein:
said rear arm includes:
a web notch.

7. The syringe control pistol of claim 1 wherein:
said front face includes:
a plurality of finger notches; and
a finger ring surrounding a plurality of finger notches.

8. The syringe control pistol of claim 7 wherein:
said rear arm includes:
a web notch.

9. The syringe control pistol of claim 1 wherein:
said front arm and said rear arm include:
cooperative stop means for stopping said arms from pivoting open past a predetermined angle.

10. A syringe control pistol for holding in a hand of a user to control the dispensing of fluid from a syringe; the syringe including: a barrel; and a plunger; the barrel including: a front end; and a rear end including an orifice having an outward flange around the orifice; the plunger including: a horizontal center axis; a front end disposed in the barrel; a midsection disposed in the orifice; and a rear end including a rear-facing, bearing surface; said pistol including:
a front arm including:
a bottom end;
a front face for receiving pressure from the fingers of the user's hand; and
a top end:
a plurality of barrel holders for holding syringes of different sizes; each barrel holder adapted for attachment to said top end of said front arm for holding a barrel of a syringe such that the barrel cannot move forward and the plunger extends rearward; said front arm and each said barrel holder including cooperating attachment means for selectively attaching and detaching said barrels;
a rear arm including:
a bottom end pivotly connected to said bottom end of said front arm;
a rear face for receiving pressure from the palm of the user's hand; and
a top end including:
a roller for bearing against the bearing surface of the plunger for pushing the plunger forward in the barrel to disperse fluid from the syringe as the user's hand squeezes said front arm and said rear arm toward one another.

11. The syringe control pistol of claim 10 wherein:
said cooperating attachment means includes:
a front-to-rear sliding attachment on said barrel; and
a rear-to-front sliding attachment on said front arm.

12. The syringe control pistol of claim 11 wherein:
said cooperating attachment means includes:
cooperating detent means for resiliently retaining said barrel holder on said front arm.

13. The syringe control pistol of claim 10 wherein:
said cooperative attachment means includes:
a sliding rod connection.

14. The syringe control pistol of claim 13 wherein:
said cooperating attachment means includes:
cooperating detent means for retaining said barrel holder on said front arm.

15. The syringe control pistol of claim 10 wherein:
each said barrel holder having a horizontal center axis substantially in alignment with said roller.

\* \* \* \* \*